United States Patent [19]
del Castillo

[11] Patent Number: 5,382,256
[45] Date of Patent: Jan. 17, 1995

[54] PROTECTIVE INSTRUMENT FOR SUTURING

[76] Inventor: Javier B. del Castillo, Sant Ferran 60, 08700-Igualada (Barcelona), Spain

[21] Appl. No.: 729,209

[22] Filed: Jul. 12, 1991

[30] Foreign Application Priority Data

Jul. 13, 1990 [ES] Spain ............................. 9002237[U]
Jun. 19, 1991 [ES] Spain ............................. 9101945[U]

[51] Int. Cl.⁶ ............................................. A61B 17/04
[52] U.S. Cl. ......................................... 606/148; 606/1; 30/324; 30/326; D7/653
[58] Field of Search ............... 606/148, 125, 139, 1; 2/21; D7/653; 30/324, 325, 326

[56] References Cited

U.S. PATENT DOCUMENTS

| | | | |
|---|---|---|---|
| D. 314,312 | 2/1991 | Richmond | D7/653 |
| 431,914 | 7/1890 | Plotts | 30/324 |
| 1,108,767 | 8/1914 | Lechner | D7/653 |
| 1,405,928 | 2/1922 | Luse . | |
| 2,467,613 | 4/1949 | Davis . | |
| 3,511,242 | 5/1970 | Agnone . | |
| 3,735,760 | 5/1973 | Vreeland, Jr. . | |
| 4,616,770 | 10/1986 | Johns . | |
| 4,784,139 | 11/1988 | Demos | 606/148 |
| 4,803,984 | 2/1989 | Naraganan et al. | 606/148 |
| 4,807,600 | 2/1989 | Hayes . | |
| 4,944,437 | 7/1990 | Calvert . | |
| 4,985,038 | 1/1991 | Lyell . | |
| 5,038,476 | 8/1991 | McCrea | 30/141 |

FOREIGN PATENT DOCUMENTS

| | | | |
|---|---|---|---|
| 793372 | 1/1936 | France . | |
| 2357 | of 1895 | United Kingdom | 30/324 |
| 9448 | of 1904 | United Kingdom | 30/326 |
| 638892 | 6/1950 | United Kingdom . | |

*Primary Examiner*—Stephen C. Pellegrino
*Assistant Examiner*—Gary Jackson
*Attorney, Agent, or Firm*—Staas & Halsey

[57] ABSTRACT

The protective instrument for suturing is formed by a rigid longitudinally concavo-convex body member having rounded edges and blunt ends. It is provided with a handle, so that in use the concave portion is facing the inner surface of the incision and the convex portion faces the viscera, organs, vessels, nerves or other parts of the patient under operation. The purpose of the instrument is to guide the suture needle in replacement of the gloved finger of the surgeon, whereby pricks in the surgeon's finger or in the patient's viscera or other organs are avoided, preventing the infections or lesions which such pricks may cause.

15 Claims, 5 Drawing Sheets

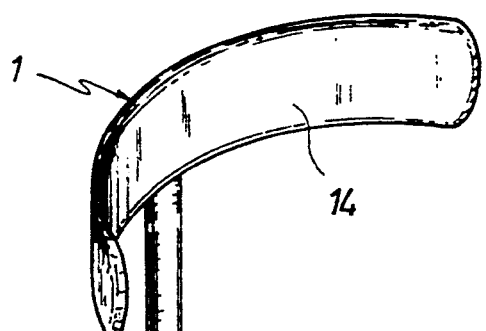
FIG. 11
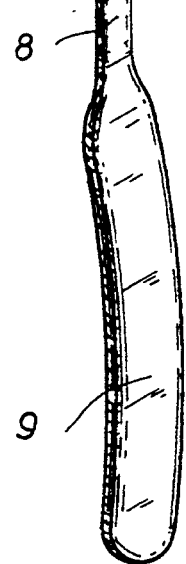
FIG. 12
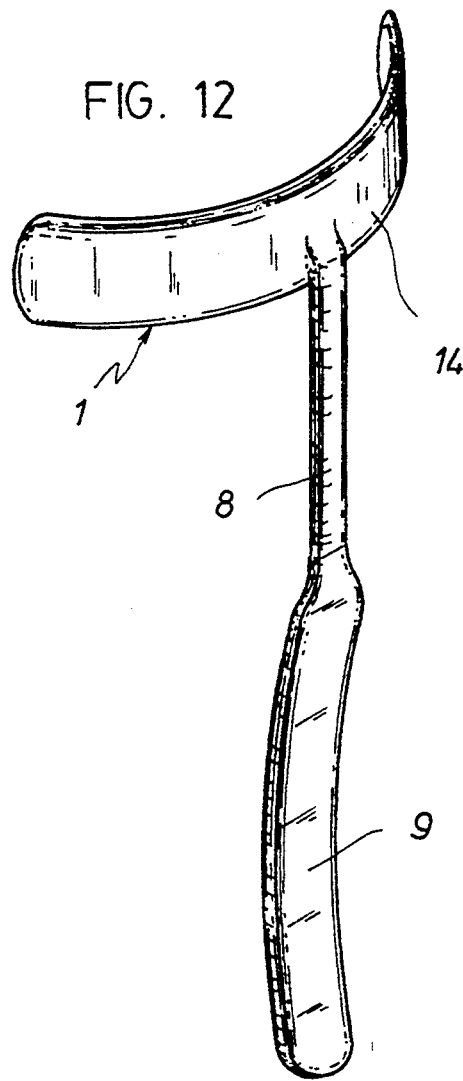

PROTECTIVE INSTRUMENT FOR SUTURING

BACKGROUND OF THE INVENTION

Field of the Invention

This invention relates to a protective instrument for suturing, particularly for protecting the surgeon's hands against possible pricks which may infect the surgeon in the case of patients suffering from infectious diseases (hepatitis, AIDS, etc) when sewing the suture for joining the two parts of an incision, as well as to avoid pricking organs, viscera or other parts underneath the said parts of the incision, as is the case of laparotomies, heart surgery, neck surgery or the like, since the tip of the needle must be detected by feeling below the first concealed portion of the wall to be joined, when this is perforated, to guide it towards the concealed portion of the second part, drawing the thread with it.

When working without any instrument, only with the gloved hand, the surgeon runs a substantial risk of pricking his finger when feeling for the invisible needle tip or of pricking a viscera, a vessel or a nerve, with the possibility of causing infections or lesions, whereby means of fortune providing some degree of protection have been used. One of such means consists of using a piece of leather or the like inserted below the envolving wall, either abdominal or any other, to retain and protect the viscera, vessels, etc. Likewise narrow sheetlike valves of malleable metal of the type normally used as incision separators are applied in the same way.

The need for such instrument protecting against pricks is expressed in the article by R. J. Heald, published in "The British Journal of Surgery" where, in the Spanish Edition of April 1991, page 278, third paragraph it is said, ". . . surgeons will have to banish the habit of using a finger of the left hand for guiding the suture needle on its way through the tissues".

The instrument of the present invention responds to the above mentioned criteria of protection, although at the same time an attempt is made to achieve greater security in leading the needle in both directions on the inside of the area of the patient's body where the incision to be sutured has been made, thereby improving the suturing job and providing, at the same time, greater security as far as the need to protect against pricks is concerned.

SUMMARY OF THE INVENTION

Consequently, the instrument in question relates to a protective instrument essentially characterised in that it is formed by a rigid longitudinally concavo-convex body member having rounded edges and blunt ends.

According to the invention, the rigid body member, which is essentially spoonlike in shape, is longitudinally curved in the direction of the concavity thereof and the concavo-convex right section tapers along the whole length towards the ends.

According to the invention, the major axis of the spoonlike body member may be a straight, broken or curved line.

According to the invention, the spoonlike body member may be asymmetrical both longitudinally and transversely.

According to the invention, the spoonlike body member is provided on the convex part thereof with direct or indirect handling and positioning means.

According to the invention, the direct handling means consists of an arrangement into which one or more gloved fingers of the surgeon or of an assistant may be inserted.

According to the invention, the direct handling means consists of an arrangement into which one or more gloved fingers of the surgeon or of an assistant may be inserted, both longitudinally and transversely of the hand.

According to the invention, the arrangement is formed by a ring dimensioned to fit one or more gloved fingers of the hand of the surgeon or of the assistant.

According to the invention the arrangement is formed by a thimble-like pocket capable of containing one or more fingers simultaneously of the surgeon or of the assistant.

According to the invention, the spoonlike body member is formed by a hollow body member having on the one hand an oval concave active surface and on the other hand a housing for the gloved hand of the surgeon or of the assistant, forming a sort of mitten.

According to the invention, the indirect handling means are formed by a handle, provided with a grip, which is fixedly attached to any part of the convex portion of the spoonlike body member, either integrally or by welding.

According to the invention, the convex portion of the spoonlike body member is provided with retaining means for insertion of the indirect handling and positioning means.

According to the invention, the retaining means arrangement contemplates several insertion points for the handling and positioning means.

According to the invention, the insertion points contemplated in the retaining means may have fixed or adjustable orientations for the insertion of one or more handling and positioning means.

According to the invention, the handling and positioning means are provided with means for retainable and removeable insertion.

According to the invention, the spoonlike body member forms the support of a sheath member elastically adaptable thereto and disposable after each use.

According to the invention, the whole instrument, or at least the spoonlike body member thereof, may be made from disposable material.

BRIEF DESCRIPTION OF THE DRAWINGS

Illustrative drawings showing the subject surgical instrument are described hereinafter.

FIG. 11 is a perspective view of a simplified embodiment of the protective instrument, seen from the concave surface.

FIG. 12 is the same instrument of the previous figure, seen from the convex side.

DETAILED DESCRIPTION OF THE INVENTION

Figure 1:
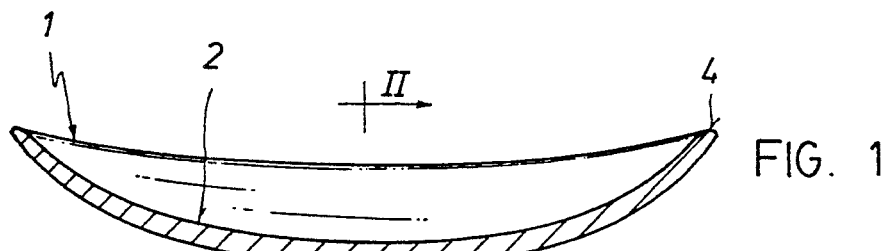
FIG. 1 is a longitudinal section view of the basic rigid spoonlike body member.
Figure 2:
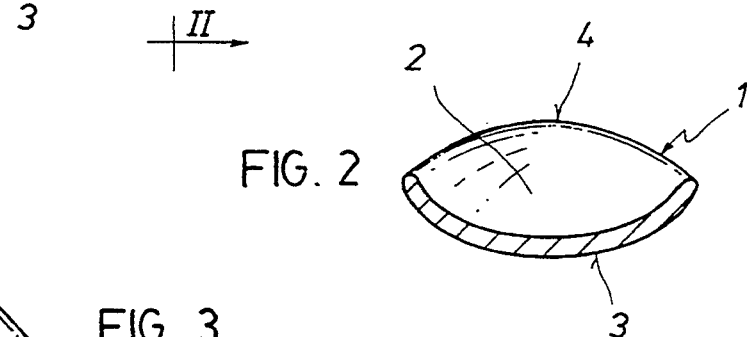
FIG. 2 is a cross section view on the line II—II of FIG. 1.

Basically, the present instrument consists of a generally longitudinally spoonlike body member, preferably curved in the direction of the concavity thereof, as shown in FIGS. 1 and 2, having an oval, elongate concave active surface 2 and a convex rear surface 3 to be associated with handling means, the ends 4 thereof being suitably rounded to avoid sharp points and so that all the edges are not sharp.

The material used for the instrument may be stainless steel, without discarding others such as titanium, tungsten, etc.

It is the spoonlike body member 1 which will be used for performing the pertinent suturing operations and with a view to achieving the proposed objectives, i.e. to avoid the operator's hands and the immediate viscera, vessels, nerves, tendons, etc. of the patent from being pricked. At the same time it facilitates adequate orientation of the needle while moving through the concealed space between the outer portion of one part of the incision and said viscera or other organs, on being guided by the longitudinal and transverse cavity of the body member to be able to sew the suture stitches with due conformity.

Several solutions allowing comfortable holding and orientation are contemplated for the use of the spoonlike body member 1 in question. Thus, pertinent means of a direct or indirect type are disposed on the convex portion 3.

Figure 3:
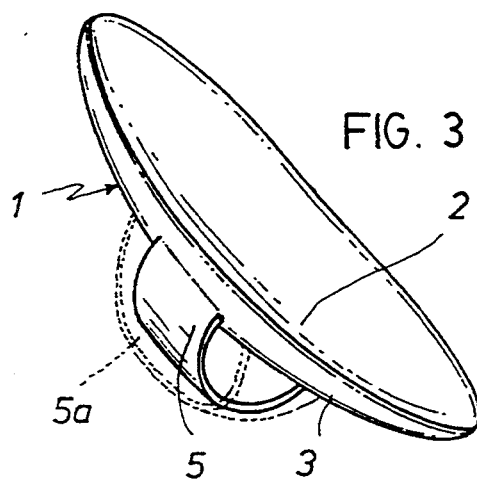
FIG. 3 shows a spoonlike body member provided with a ring shaped insertion arrangement for holding on the convex side thereof.
Figure 4:
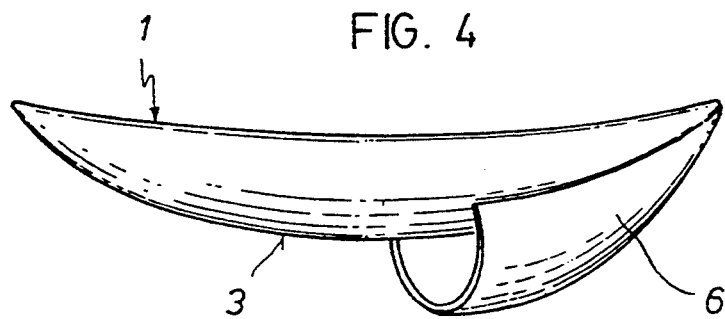
FIG. 4 shows a spoonlike provided with a pocket shaped insertion arrangement.

In the case of direct handling means for said spoonlike body member 1, an insertion arrangement such as a ring 5 or 5a is used, orientated transversally or longitudinally of the body member, respectively, allowing snug fitting of one or more of the surgeon's or assistant's fingers, as shown in FIG. 3. In another case, the spoonlike body member 1 appears as a pocket 6 for insertion of one or more fingers, whereby it is thimble-shaped as shown in FIG. 4. Likewise, the spoonlike body member 1 is presented in form of a mitten 7 which has, on the one hand the active arrangement 2 and on the other hand is provided with a housing adapted for receiving the gloved hand of the surgeon or of the assistant, as shown in FIG. 5.

Figure 5:
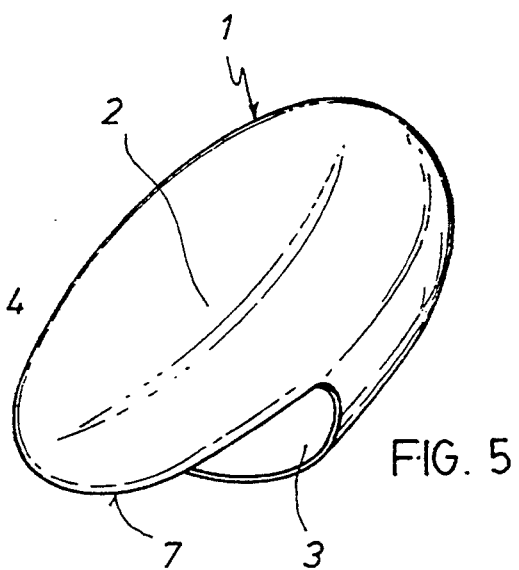
FIG. 5 shows a spoonlike body member forming a mitten-like housing for the hand.

In the cases shown in FIGS. 3, 4 and 5, the active portions 2 of the body member cover an extension of the hand sufficient for the protection sought, without prejudice to the operativity thereof.

Figure 6A:
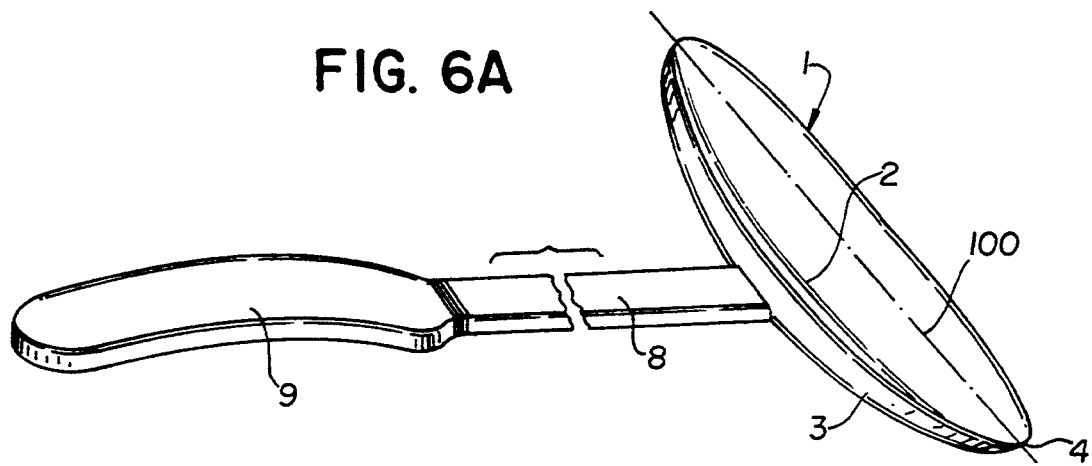
FIG. 6a is a perspective view of a spoonlike body member having a major axis defined by a straight line and connected to a handle with grip.
Figure 6B:
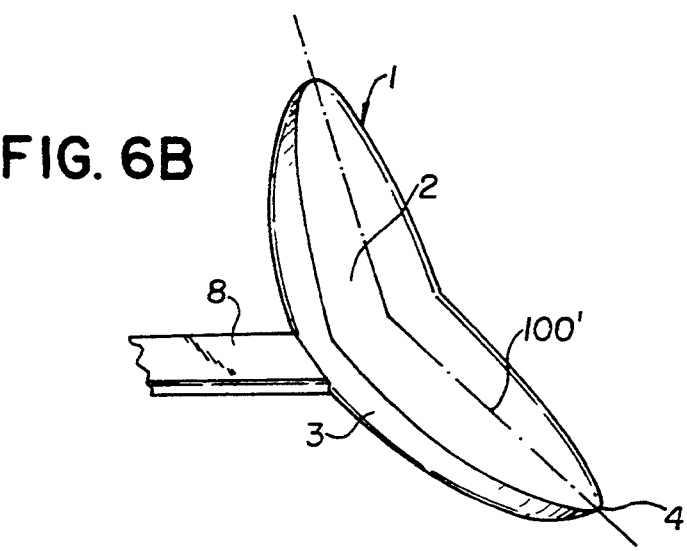
FIG. 6b is a perspective view of a spoonlike body member having a major axis defined by a broken line.
Figure 6C:
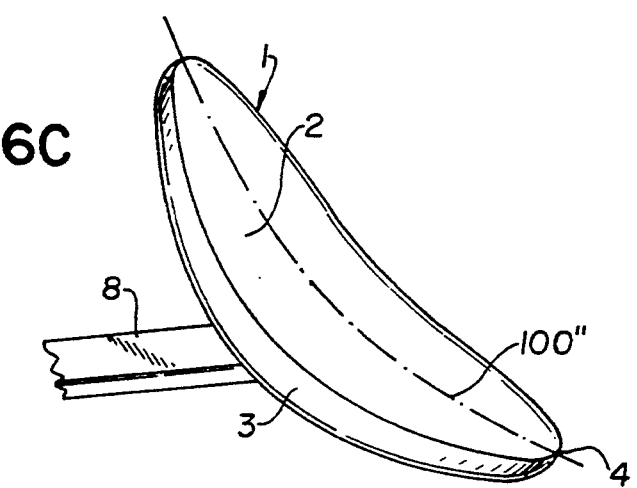
FIG. 6c is a perspective view of a spoonlike body member having a major axis defined by a curved line.
Figure 7:
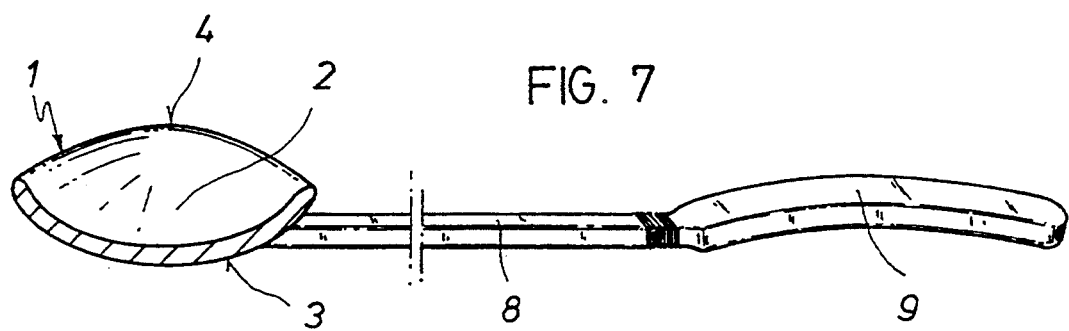
FIG. 7 is a cross section view of the body member of the previous figure.
Figure 8:
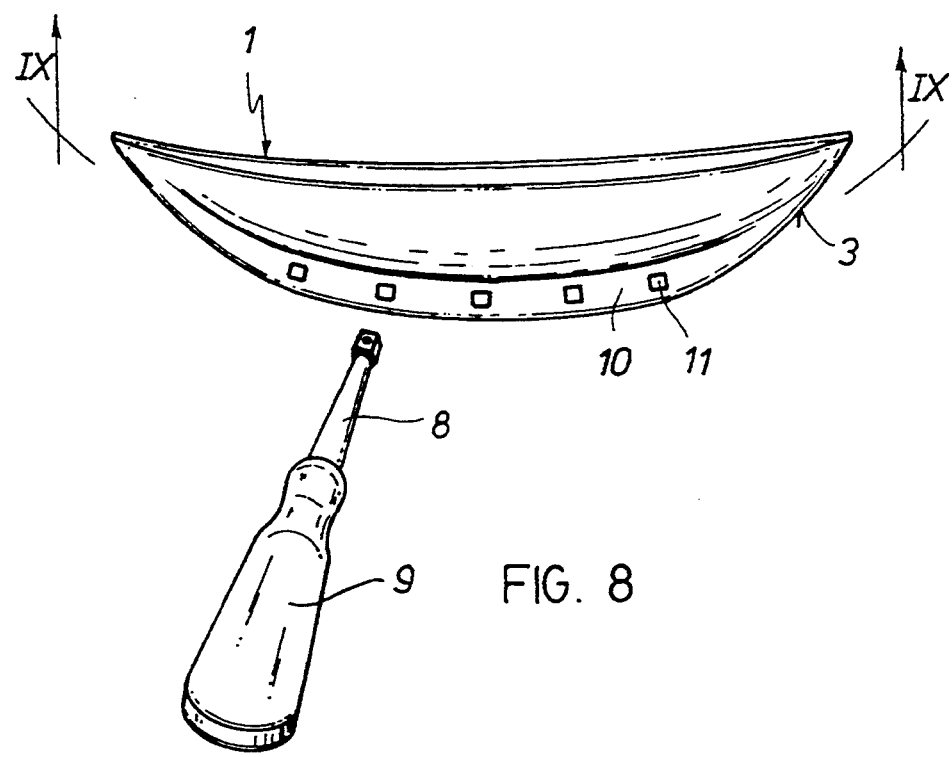
FIG. 8 shows a spoonlike body member having an arrangement for retaining a handling and orientation means in form of a handle with grip.
Figure 9:
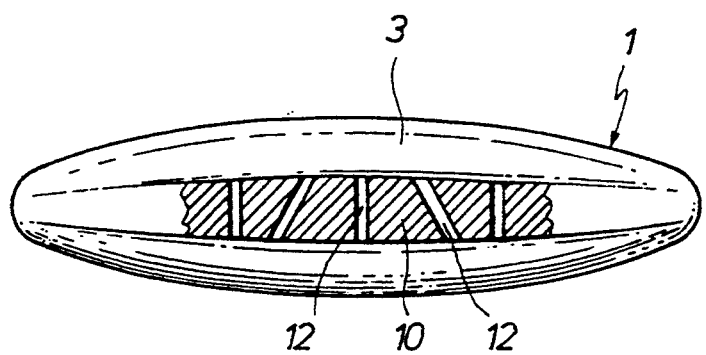
FIG. 9 is a cross section view on the line IX—IX of FIG. 8.

With regard to the indirect handling means for the spoonlike body member 1, the holding member consists of a certain type of handle 8, provided with a grip 9 which is fixedly or removably attached to the body member, in all cases without possibility of rotation. In this case, one solution is as shown in FIGS. 6 and 7, where the said body member 1 is attached laterally to the handle 8. In FIG. 6, body member 1 has a major axis 100 defined by a straight line. Alternatively, as shown in FIG. 6a, body member 1 may include a major axis defined by a broken line 100', or, as shown in FIG. 6b, body member 1 may include a major axis defined by a curved line 100''. In another case, see FIG. 8, the body member is provided with a protuberance 10 on the convex side 3 thereof for coupling with the handle 8, possibly adjustably. The fixed attachment may be by welding and the removable connection may be by way of one or more orifices 11. Where several orifices 11 are available, the handle may be located in the most convenient position in each case. Furthermore, according to FIG. 9, the protuberance 10 may have insertion means 12 for the handle 8, with different orientations to be selected in each case.

Figure 10:
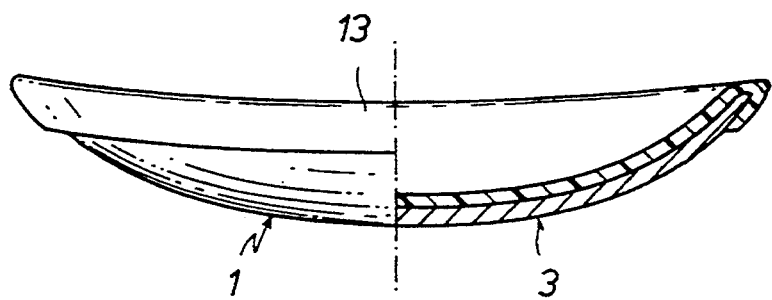
FIG. 10 is a view, partly in section, of a spoonlike body member provided with an elastically adjustable, disposable functional sheath.

Optionally, all of the protective instrument, or at least the spoonlike body member 1, may be of the disposable type after a single use. Another equivalent solution is to provide the spoonlike body member 1 with a functional sheath 13 adaptable to the active surface and adapted to be disposed of after use, as shown in FIG. 10.

A simplified embodiment is shown in FIGS. 11 and 12, where the rigid body member 1 is formed by a sheetlike member 14 having blunt ends and rounded edges to avoid sharp edges which could damage the patient's tissues, organs, viscera or vessels. It is provided with handling means which, in the embodiment shown, consist of a handle 8 and a grid 9.

Although the body member 1 is shown to have a spoonlike form in the drawings, an elbowed shape is also feasible, with equal or unequal arms and with a constant width or otherwise. The spoonlike body member may also be of different sizes.

The protective instrument of the invention affords the desirable protection both for the operator, in that it prevents contaminating pricks, and for the patient, in that it prevents possible pricks in the viscera or other parts and the consequent complications because of infection or other causes. At the same time, the function consisting of guiding the needle in the correlative suture stitches is of interest, bearing in mind that the tip of the needle is concealed and operates in an area which is also hidden from sight under the wall of the two parts to be joined.

The instrument is used by placing it over the viscera or other organs through the incision made in the wall to be closed by suture. It is pressed against said viscera or other organs and, in general, in the transverse direction of said incision, overlapping the parts to be joined on the inside.

Thus, when the needle penetrates through the wall, it meets the concave active surface of the body member, whereby it encounters an obstacle for advancing forward and, furthermore, by the concavity of the body member it will be orientated towards the other part of the wall to be perforated from the unseen inside face.

The successive stitches will be made in accordance with the technique advisable in each case. One way is to knot the stitches from one end to the centre third of the length of the suture, leaving the last two stitches untied, after which knotting is started from the other end in the same way as before. Whereby it is possible to remove the spoonlike body member, the stitches of the centre third being then finally knotted.

What I claim is:

1. A protective instrument for suturing, comprising:
a rigid concavo-convex body member having a concave portion, a convex portion, and a rounded peripheral edge, said rigid body member extending in a longitudinal direction that terminates in blunt ends; and
handling and positioning means, including a handle and a grip, said handle connected to said rigid body member and extending in a direction that is other than said longitudinal direction of said rigid body member, said handling and positioning means being attached to the convex portion of the rigid body member.

2. A protective instrument for suturing as recited in claim 1, wherein said ends of said rigid body member are at a higher level than other portions of said rigid body member so that said edge between said ends is longitudinally curved in the direction of the concavity of said rigid body member, and the concavo-convex cross section tapers from a middle portion of said rigid body member along the whole length towards said ends.

3. A protective instrument for suturing as recited in claim 2, wherein said rigid body member includes a major axis defined by a straight line.

4. A protective instrument for suturing as recited in claim 2, wherein said rigid body member is asymmetrical in at least one of the transverse direction and said longitudinal direction.

5. A protective instrument for suturing as recited in claim 2, wherein said handling and positioning means is fixedly attached to and integrally formed with said convex portion of said rigid body member.

6. A protective instrument for suturing as recited in claim 2, wherein said convex portion of said rigid body member is provided with retaining means for inserting said handling and positioning means.

7. A protective instrument for suturing as recited in claim 6, wherein said handling and positioning means includes means for retaining and removing said handling and positioning means from said rigid body member.

8. A protective instrument for suturing as recited in claim 6, wherein said retaining means includes several insertion points for insertion of said handling and positioning means.

9. A protective instrument for suturing as recited in claim 8, wherein said insertion points of said retaining means have fixed orientations for the insertion of at least one of said handling and positioning means.

10. A protective instrument for suturing as recited in claim 8, wherein said insertion points of said retaining means have adjustable orientations for the insertion of at least one of said handling and positioning means.

11. A protective instrument for suturing as recited in claim 2, wherein said rigid body member includes a major axis defined by a broken line.

12. A protective instrument for suturing as recited in claim 2, wherein said rigid body member includes a major axis defined by a curved line.

13. A protective instrument for suturing as recited in claim 2, wherein said handling and positioning means is fixedly attached to said convex portion of said rigid body member by welding.

14. A protective instrument for suturing as recited in claim 1, wherein said handle extends in a direction substantially orthogonal to said longitudinal direction of said rigid body member.

15. A protective instrument for suturing as recited in claim 1, wherein the width of said rigid body member extending along the transverse direction is substantially constant in a central portion of said rigid body member between said ends.

* * * * *